(12) United States Patent
Mirhoseini et al.

(10) Patent No.: US 9,192,703 B2
(45) Date of Patent: Nov. 24, 2015

(54) INTELLIGENT NANOMAGNETIC CARDIAC ASSIST DEVICE FOR A FAILING HEART

(71) Applicants: Mahmood Mirhoseini, Germantown, WI (US); Mary Cayton Mirhoseini, Germantown, WI (US); Aria Manasheri, Germantown, WI (US)

(72) Inventors: Mahmood Mirhoseini, Germantown, WI (US); Mary Cayton Mirhoseini, Germantown, WI (US); Aria Manasheri, Germantown, WI (US)

( * ) Notice: Subject to any disclaimer, the term of this patent is extended or adjusted under 35 U.S.C. 154(b) by 0 days.

(21) Appl. No.: 14/662,199

(22) Filed: Mar. 18, 2015

(65) Prior Publication Data

US 2015/0190562 A1    Jul. 9, 2015

Related U.S. Application Data

(63) Continuation-in-part of application No. 13/244,423, filed on Sep. 24, 2011, now abandoned.

(51) Int. Cl.
| | |
|---|---|
| *A61N 1/362* | (2006.01) |
| *A61M 1/10* | (2006.01) |
| *A61M 1/12* | (2006.01) |
| *A61F 2/24* | (2006.01) |

(52) U.S. Cl.
CPC ............ *A61M 1/1046* (2013.01); *A61F 2/2481* (2013.01); *A61M 1/1055* (2014.02); *A61M 1/1068* (2013.01); *A61M 1/122* (2014.02); *A61F 2250/0001* (2013.01)

(58) Field of Classification Search
CPC ... A61M 1/1068; A61M 1/122; A61F 2/0045; A61F 2/0063; A61F 2002/068
USPC ....................................... 600/16, 17
See application file for complete search history.

(56) References Cited

U.S. PATENT DOCUMENTS

| | | | | |
|---|---|---|---|---|
| 6,887,192 | B1 * | 5/2005 | Whayne et al. ................. | 600/16 |
| 7,338,436 | B1 * | 3/2008 | Snell et al. ...................... | 600/37 |
| 2009/0292160 | A1 * | 11/2009 | Nieman .......................... | 600/16 |

* cited by examiner

*Primary Examiner* — Allen Porter, Jr.
(74) *Attorney, Agent, or Firm* — Barry Choobin; Patent 360

(57) ABSTRACT

The present invention is directed to a contractible and expandable jacket configured to encase at least a portion of a patient's heart. The jacket has a plurality of individual contractile cells with each of the cells having a first electrically conductive coil and a second electrically conductive coil spaced from the first coil. The first coil preferably defines at least in part a first periphery of an inner nucleus of the cell and the second coil preferably defining at least in part an outer portion of the cell spaced outwardly from the inner nucleus. When electrical current passes through the first and second coils in opposite directions, the cell contracts and when electrical current passes through the first and second coils in the same direction the cell expands. Each of the individual cells has conductive appendages for conducting information to and from the individual cells.

10 Claims, 3 Drawing Sheets

INTELLIGENT NANOMAGNETIC CARDIAC ASSIST DEVICE FOR A FAILING HEART

RELATED APPLICATION

This application relates to and claims priority from provisional application Ser. No. 61/389,996, filed on Oct. 5, 2010, and Non-provisional Ser. No. 13/244,423 the contents of which are incorporated herein in its entirety.

BACKGROUND OF THE INVENTION

This invention is generally directed to the treatment of patients with heart failure and specifically relates to cardiac assist devices and systems and the use thereof for such treatments.

Heart failure as a result of end stage coronary artery disease, or other cardiac conditions, is an increasingly prevalent problem. The costs associated with frequent hospital admissions, medications, and outpatient visits are staggering, and is estimated at almost $30 billion per year for the United States alone. Heart failure currently accounts for 6.5 million hospital days annually in the United States, 12-15 million office visits, and is the most frequent primary diagnosis for hospitalization. There are approximately five million people diagnosed with heart failure in the United States, and with an increasingly aging population, the absolute number of patients is increasing with about 550,000 people being newly diagnosed each year. It is estimated that as people approach 65 years of age, the number of people with heart failure is 10 per 1000 in the population. Despite advances in both diagnostic methods and treatment alternatives, the mortality for late stage heart failure, in symptomatic patients, approaches 50% at one year. For those with mild disease, the mortality rate is 50% within 4-5 years.

The heart failure is defined as a complex clinical syndrome that can result from any structural or functional cardiac disorder that impairs the ventricular filling and/or ejection of blood to the body. Manifestations of heart failure include dyspnea, fatigue, exercise intolerance, and fluid retention. Heart failure can also lead to pulmonary congestion and peripheral edema. Usually systolic and diastolic dysfunction co-exist. Neuro-hormonal factors may be altered and hemodynamic stresses increased. In late stage heart failure Left Ventricular (LV) filling pressures are increased and the QRS of the electrocardiogram may be widened. In addition, there may be refractory volume overload, decreased peak oxygen uptake with exercise, decreased cardiac output, narrow pulse pressure, tachycardia at rest, cool extremities, renal dysfunction, and altered mentation.

The causes of heart failure are many, the diagnosis is complex, but the fundamental hemodynamics are the same. There is an imbalance between cardiac output and the needs of the body. The imbalance of blood flow is associated with water retention resulting in central and peripheral edema. Moreover, a failing heart undergoes structural changes from the normal elliptical shape, namely, the heart dilates, and assumes a spherical shape. The ability to maintain adequate cardiac output is reduced. The degree of severity in reduced ejection fraction varies depending on how severe the heart failure is. As a result of spatial changes, the heart valves can become incompetent. The normal elasticity of the heart muscle is reduced or lost. The changes also lead to instability of the normal electrical function of the heart.

The American College of Cardiology and American Heart Association classified heart failure in four main categories, stage A and B are patients at risk or predisposed to failure, stage C is patients with current or past symptoms, and in stage D the patients have truly refractory or late stage failure. The treatment for heart failure is continually evolving. Patients in stages A, B, and C can usually be managed with effective pharmacological treatment and/or treatment of symptoms. Stage D patients may be eligible for specialized or advanced treatments which can include mechanical support, fluid removal, continuous inotropic support, cardiac transplantation, or innovative and experimental procedures.

Cardiac support devices monitor ventricular filling pressures and hemodynamic variables. They are designed to optimize LV filling pressures. In theory the devices alter physical stresses on the LV, and perhaps improve performance, and may prevent further ventricular dilation. Wrapping devices allow muscle shortening and resist circumferential expansion beyond the limits of the wrap. They serve as a constraining factor and give support to the heart.

Goals when implanting devices include improved blood flow, restoration of geometric and functional LV function, reshaping, and restoration of anteroapical and septal regions. Additional goals include enhancing the ability to generate force and muscle shortening, improve systolic and diastolic function, and to manage physiological factors of blood pressure, heart rate, blood volume, reduce ischemia, and to reduce filling pressures both at rest and with exertion.

At present, cardiac transplantation is the only established surgical treatment for end stage heart disease and cardiac failure. However, transplantation is available to less than 2500 patients in the US annually, a small fraction of patients with diagnosed end stage disease is considered. An innovative device designed to help refractory patients is needed.

Heart failure as a result of end stage heart coronary artery disease, or other cardiac conditions, is extremely prevalent, and the incidence is increasing annually. The costs associated with frequent hospital admissions, medications, outpatient visits, and other interventions are staggering. A method to ameliorate and/or reduce individual disability and the associated financial burden would benefit both the patients and society in general.

At the present time, heart failure accounts for more than 1 (one) million hospitalizations annually in the United States. More than 5 million people have a diagnosis of heart failure in the country, and with an increasingly aging population the absolute number of patients is increasing progressively.

Despite advances in diagnostic methods and treatment alternatives, the mortality of late stage disease, in symptomatic patients is estimated to be 50% at one year. For those with less severe disease the mortality is 50% within 4-5 years.

The causes of heart failure vary, depending on the underlying cardiac condition, but the fundamental defect is the same, an imbalance of blood supply from the heart to meet bodily demands. A failing heart undergoes structural changes, dilates, and assumes a spherical rather than elliptical shape. As a result of spatial changes the heart valves sometimes become incompetent. Spherical shapes lead to cardiac dysfunction, the mechanically efficient and electrically stable elliptical shape is lost.

A failing heart also suffers from a loss of elasticity, which means the pumping function to meet the needs of the body is inefficient or lost. Although a number of invasive procedures have been employed to remedy this condition, and new more effective medications have been developed, a fully satisfactory method of treating this very complex condition is not available.

Conventional approaches to the treatment of end stage disease and heart failure include medical treatment, interventions such as intra-aortic balloon pump, heart transplantation, and excision of non-contractile cardiac muscle. Experimental procedures include cardiomyoplasty and wrapping and supporting the heart.

Medical Treatment

The duration of effectiveness of medication varies, and often major side effects occur. Medication is a choice for Stages A and B heart failure, and can contribute to alleviating symptoms in stage C. In stage D, severe failure, medications are ineffective. There are no medications to force the myocardium with no contractile strength to perform effectively.

Intra-Aortic Balloon Counterpulsation

Intra-aortic Balloon Counter-Pulsation (IABP) is only effective on a very limited and temporary basis. It is not intended for long term use. Inflation and deflation of the balloon, which is usually inserted into the aorta percutaneously through the femoral artery, increases blood flow to the coronary arteries. In general, an increase of 10-20% in contractile function can be achieved. Morbidity increases with each day the balloon is in place, and includes obstructed blood flow to the affected limb, coagulopathy, infection, and malfunction of the inflation-deflation functions of the balloon.

Heart Transplantation

Heart transplant, as an option, is limited by the number of donor hearts available, and by the age and co-morbidity of the recipient. Following transplant, life long immune suppression therapy is required. Frequent medical follow-up is necessary, to evaluate effectiveness of immunosuppressive therapy and to monitor overall progress. The cost of medication and follow-up is high. Transplant rejection is always a consideration. Arteriosclerotic coronary artery disease in the transplanted heart is known to occur, and affects long term results.

Batista Procedure

In the Batista Procedure non-contractile muscle of the left ventricle is excised in order to increase cardiac output. The procedure is controversial, and the results are open to debate.

Cardiomyoplasty

Cardiomyoplasty involves an extensive surgical procedure. The latissimus dorsi muscle is dissected, lifted, and wrapped around the heart. Electrical stimulation of the implanted muscle results in muscle contraction, creating pressure on the ventricle, thereby increasing cardiac output. Because of the complexity and extent of the procedure it is only suitable for the most severe cases of heart failure. Pacemakers required for electrical stimulation of the muscle are costly. Extensive follow-up and care following the procedure is required.

Artificial Heart

A suitable artificial heart has yet to be developed, in spite of years of experimentation with varying models. One of the biggest obstacles is the incompatibility of the blood to device interface. The interface causes coagulation disturbances. External systems required to support the device and pumping mechanisms, are tethered to wall outlets, are large, and limit patient activity. There is high morbidity associated with the total artificial heart. Temporary assist devices, designed for use until a suitable donor heart can be found for permanent transplant, have many of the same drawbacks as the artificial heart.

Binding or Wrapping the Heart

A number of mechanical devices for increasing cardiac output and assisting the failing heart consist of a means such as wraps to compress the epicardial surface of the patient's myocardium. Various models and designs of cardiac wraps have been proposed, including wrapping the heart with a mesh or biocompatible material. Some cardiac wraps are inflatable so they can be inflated and deflated cyclically in response to cardiac parameters, In essence the principle of most wrapping devices is similar, to affect LV systolic pressure. In failure the end-diastolic pressure-volume (EDPVR) is altered. Right ventricular (RV) diastolic function is impaired. Wrapping does not increase diastolic function. Unfortunately, many binding or wrapping techniques do not consider septal motion, ventricular wall motion, chamber dynamics, and overall cardiac function.

Dynamic mechanical heart assist devices consist of wrapping the heart with two layers rather than one. The inner layer conforms to the epicardial surface of the heart throughout systole and diastole by means of a mechanical control system that inflates and deflates the inner wrap. The dynamic method provides enhanced support to the failing heart by closer regulation of cardiac function. The liner allows compression and relaxation of the cardiac muscle. The two layer device usually requires tubes, connected to the compression mechanism, to extend externally, outside the body, to access ports. Management of cardiac parameters is achieved mechanically by increasing or decreasing the amount of fluid in the liner. To acquire full knowledge of hemodynamics, direct pressure readings, echocardiographic evaluation, and other expensive and time consuming diagnostic tools are required.

DESCRIPTION OF EMBODIMENTS OF THE INVENTION

Figure 1:
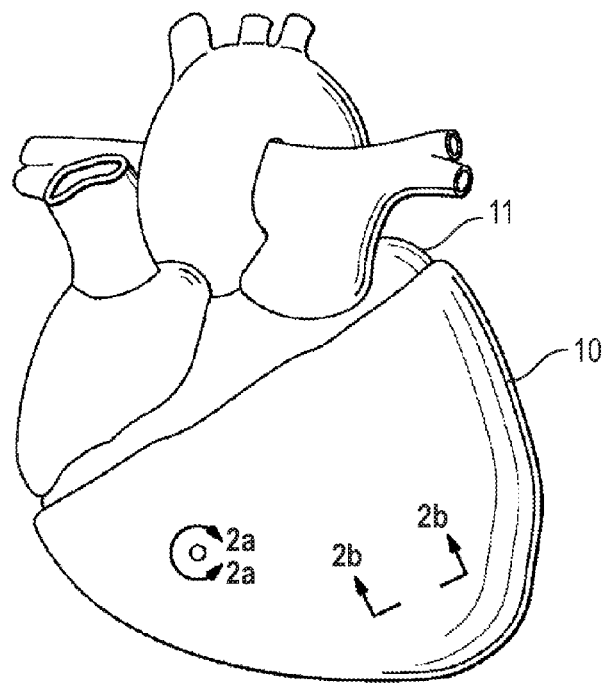
FIG. 1 is an elevational view of a patient' heart having a cardiac jacket embodying features of the invention.
Figure 2A:
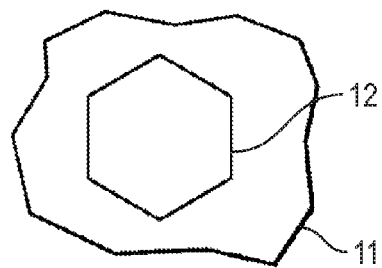
FIG. 2a is an enlarged view of region 2a-2a shown in FIG. 1.
Figure 2B:
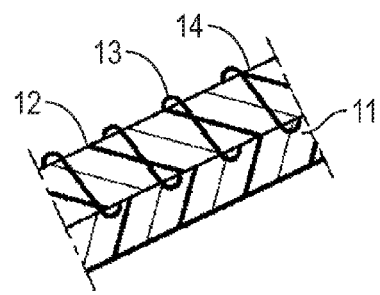
FIG. 2b is a transverse cross section of the jacket shown in FIG. 1 taken along the lines 2b-2b.

This invention is directed to an innovative device, system and method for treating a patient's heart and particularly to a cardiac wrap or jacket configured to provide improved cardiac contraction and expansion. This invention utilizes the concept of a contractile cardiac jacket which has a contractile polymer jacket with the ability to compressed a patient's heart. FIG. 1 illustrates the contractile polymer jacket 10 mounted on a patient's heart 11. The contractile polymer jacket 10 has a plurality of contractile cells 12 as shown in FIGS. 2a and 2b, preferably hexagonal in shape, that are embedded in or otherwise secured to a polymer layer of the jacket 10. The contractile cells 12 secured to the polymer layer have electrically conductive coils that are preferably made of nano-sized wires (herein termed nanowires) 13 which are wrapped in coils 14 and are incorporated in the cells 12. The nanowires 13 are preferably formed of platinum or conductive platinum alloys. The high quality of the polymer allows it to fill the spaces, between the electrically conductive coils. The polymer readily transmits the magnetic field, but does not allow the cells to stick together. The contractile polymer jacket 10 is configured to fit about a portion of a patient's heart 11 as shown in FIG. 1 and is preferably either global or elliptical in shape. While the jacket 10 is shown surrounding the patients ventricles, the jacket 10 can extend to atrial. The jacket 10 preferably also has an insulating outer layer, as shown in FIG. 1 that prevents external magnetic field interference or noise. The insulating layer is preferably made of a conductive electroactive polymer, such as a polymer having conductive carbon, platinum, gold or a conductive sulfate incorporated therein.

The electrically conductive coils are preferably formed from a conductive wire, e.g. platinum, about 30-200 nanometers. The wire is formed into a helical coil having an outer transverse dimension of about 200 nanometers to 10 micrometers in transverse dimension. The individual coils are designed to carry a current of about 2 to 20 milliamperes, preferably about 4 to about 10 milliamperes. The total electrical current to all of the contractile cells secured to the polymer layer of the jacket is about 50 to about 300 milliamperes, preferably about 100 to about 200 milliamperes, to reduce battery drainage.

Figure 5:
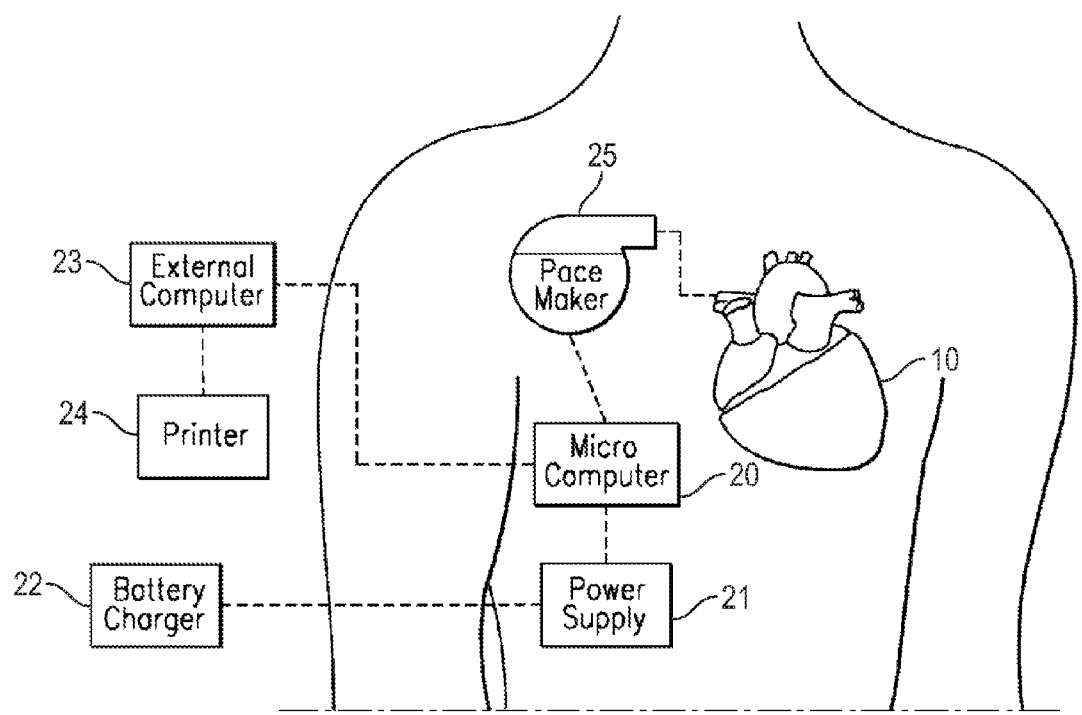
FIG. 5 is a schematic view of a patient with a cardiac jacket and control system embodying features of the invention.

A system is shown in FIG. 5 which embodies features of the invention and has a contractile jacket 10 which is controlled by microprocessor 20, preferably a field programmable gate array microprocessor. The microprocessor 20 receives signals from the right atrium (RA), right ventricle (RV), or left ventricle (LV). Important cardiac hemodynamic parameters are monitored and stored. If a pacemaker 25 is implanted, the microprocessor 20 receives signals from it. The electrical power supply 21 is preferably a small implantable battery 22, and most preferably a battery that can be recharged externally through the skin. The entire assembly is implanted in the patient. All components are biocompatible. There are no external ports, which could act as a source of infection, and there is no blood/device interface that could cause coagulation problems. Patients can be as physically active as their condition allows, and are not tethered by any external devices. The microprocessor is connected to an external computer 23 and a printer 24.

A device and system embodying features of the invention are particularly directed to a fully implantable contractile jacket with nano-sized electromagnetic coil system for assisting the failing heart. A cardiac jacket will be implanted about the patient's heart along with devices to monitor cardiac parameters and activate the device according to the cardiac parameters monitored. Contraction and expansion of the contractile jacket is regulated electronically, not mechanically, and there are no requirements for a fluid injection system. The system is completely controlled electronically.

A system embodying features of the invention comprises several components and concepts, namely:
1) An outer polymer layer with a plurality of embedded or otherwise secured contractile and expandable (relaxable) cells having at least first and second electromagnetic coils
2) Preferably an inner insulating layer around the surface of the heart to minimize or prevent the effects of external magnetic fields from the cells in the outer polymer layer on conductive heart tissue
3) A microprocessor to give commands and relay signals from:
   a) heart to computer
   b) computer to outside power source
   c) computer to individual contractile cells
4) A battery pack or power supply, preferably an internally deployed battery or power supply that is externally rechargeable through the skin
5) If needed, a two chamber (AV sequential) pacemaker or a three chamber pacemaker Preferably, internal working components of the system have no significant contact with blood.

Contractile Polymer Layer

A polymer layer that is both contractile and expandable surrounds the epicardial surface of the heart. It is made of very good quality, preferably polymeric material that readily transmits the electromagnetic field from the electrically conductive coils, resulting in contraction and relaxation or expansion from the contracted configuration of the layer. As the polymer layer contracts, it fills the spaces between the coils, preventing the coils from sticking or adhering to one another. The coils and their membrane attract each other but never stick together. Depending on the electromagnetic charge, the coils and their membranes either attract or repel each other. The inner contractile layer of jacket covers the surface of the heart and protects the coronary arteries and the heart muscle.

Either a global shaped or an elliptical shaped cardiac jacket is chosen by defining the shape of the heart. Inserting the jacket requires access to the heart, and will usually be done through a left thoracotomy, with a limited incision. In the instance of advanced or late stage heart failure with extreme remodeling of the heart muscle, a global shape is usually chosen to more closely correspond to the shape of the patient's heart. To determine the size of jacket to use, the volume of the heart is calculated from the equation $V=4/3\ R^3$. The shape and size of the heart may also evaluated by 30 echocardiogram or 30 magnetic resonance imaging (MRI).

Figure 3:
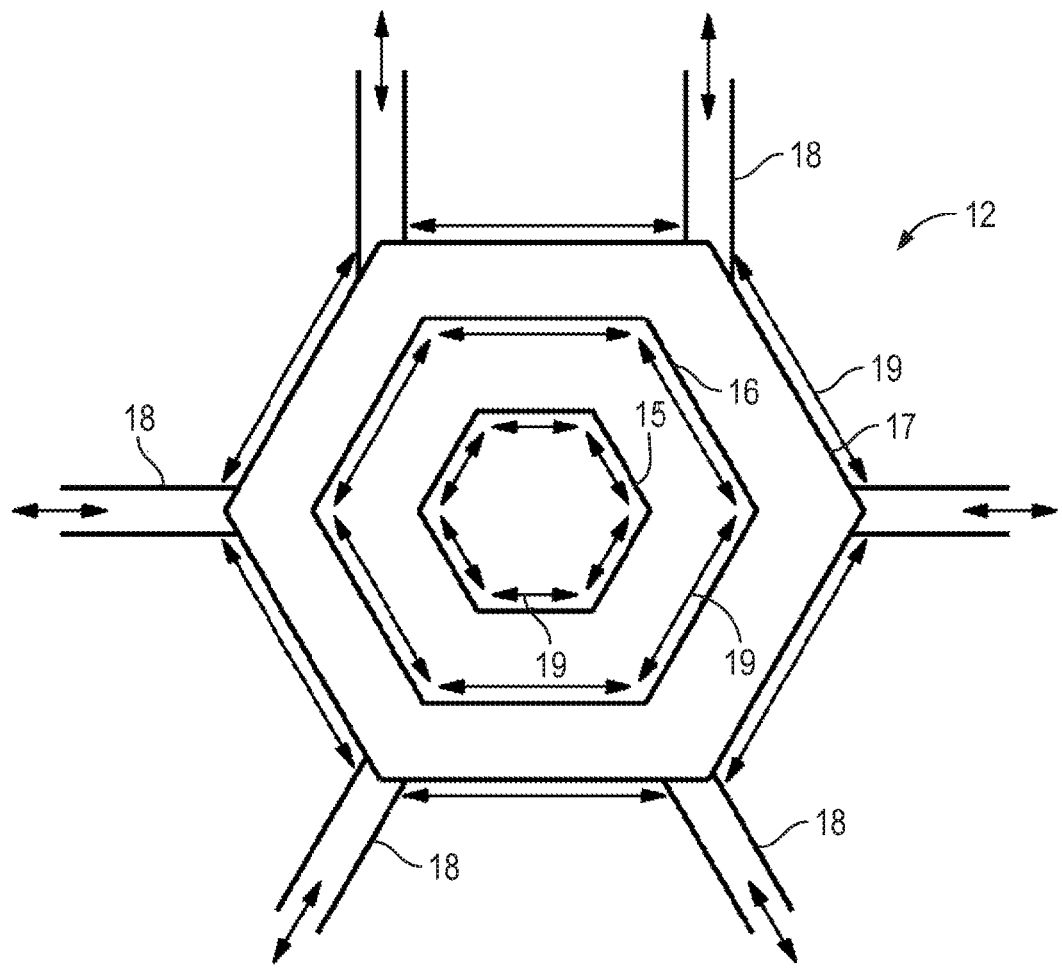
FIG. 3 is a plan view of a cell of the jacket shown in FIG. 1.

In accordance with embodiments of the invention, contractile magnetic cells with nano-sized coils are embedded in or secured to the inner polymer jacket. A typical contractile cell 12 is schematically shown in FIG. 3 and is preferably hexagonal in shape. The number of cells can vary, and may be tailored for each individual patient based on the surface area of the heart. Surface area can also be determined by the 30 echocardiogram or 30 MRI. The number of nano-sized cells embedded in or otherwise secured to the inner polymer jacket can range from a few hundred to millions depending upon the size of the individual cells, the size of the patient's heart and various processing parameters. The surface area of the heart is calculated by: $S=4\pi R^2$.

The nano-sized cells 12 communicate with each other and receive information about hemodynamic parameters. Upon expansion or relaxation of the cardiac jacket 10 from the contracted configuration, the heart fills with blood, and upon jacket contraction, blood is expelled from the heart chamber to the patient's body. The nano-sized cells 12 may work sequentially or in unison to effect contraction or expansion of the patient's heart.

Magnetic Contractile Cells

As shown in FIG. 3, each hexagonal nano-sized cell 12 has a body, or outside core, inner core, and a nucleus. The divisions between the nucleus and bodies are referred to as membranes. The preferred hexagonal shape is retained by the nucleus. The periphery of the nucleus is defined at least in part by a first electrically conductive coil 15. The inner core has a periphery defined by a second electrically conductive coil 16. The outer core has a periphery defined at least in part by a third electrically conductive coil 17. The cells 12 are interconnected by communicating channels 18 located at the angles of the hexagon in the individual cells. The cells 12 preferably work in unison or sequentially.

Figure 4:
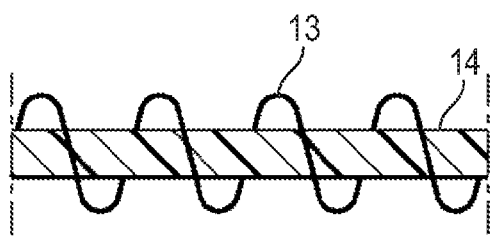
FIG. 4 is a transverse cross section of the cell shown in FIG. 3.

Each line or periphery of the hexagon, inner and outer core, and nucleus, 14 is wrapped with a coiled, nano-sized platinum wire 13 as shown in FIG. 4. The electrically conductive coils 15, 16, 17 are secured along each line of the hexagonal shaped cell and follow the line continuously around the hexagon, preferably encompassing both the inside and outside of the polymer layer. The nucleus bound by the first conductive coil 15 is stationary. The electrical current in the first coil 15 remains in the same direction and generates a magnetic field in a first direction.

Figure 6:
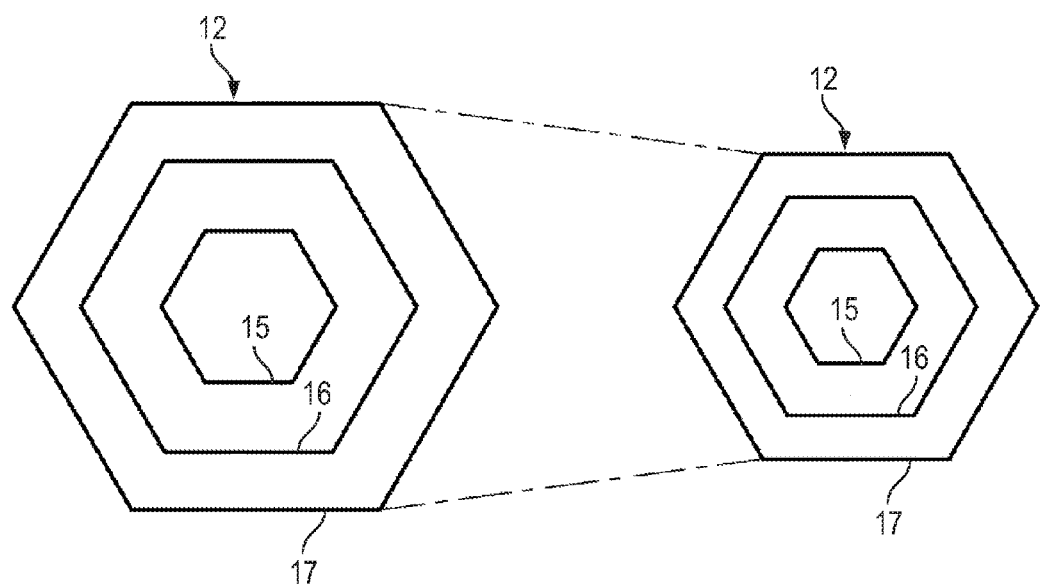
FIG. 6 illustrates a cell in an expanded configuration and a contracted configuration.

The current in the second conductive coil 16 can sequentially be in the same and opposite directions and preferably change directions in time to the patient's pulse, creating a magnetic field that is sequentially in the same and opposite directions as the nucleus. This provides the contraction or expansion of the cell 12 such as shown schematically in FIG. 6. Contraction of the jacket ejects blood from the patient's heart into the body and expansion or relaxation of the jacket from the contracted configuration allows the heart chambers to fill with blood. The electrical current in the third electrically conductive coil 17 is essentially in the same direction as the electrical current in the first electrically conductive coil 15 so as to augment the contraction and expansion of each individual contractile cell 12.

The tiny, nano-sized wires of the cells are preferably wrapped by robotic means. The wire wrap of the nucleus is stationary, but the current in the coil wrapped membrane portion of the hexagon can change directions. The directional current change in the second coil 16 creates changes in the direction of the magnetic field. The direction of the change is either in the same direction as the current in the coil of the nucleus, or in the opposite direction. When current movement in the second coil 16 of the inner core is in the same direction the first coil 15 of the nucleus, the coils are repelled, and the cell expands. Repelling or attraction of the cell 12 is characterized by ++ or −−. When the magnetic field generated by the second coil 16 is in the opposite direction from the direction of the coil of the nucleus, attraction occurs, causing contraction of the cell 12, and characterized by ±±. Similar movement occurs between the second coil 16 and the third coil 17 due to the current flow being the same or opposite therethrough. Contraction of the cells 12 causes the jacket 10 to contract and squeeze the heart, ejecting the blood from the LV. When the cells are repelled, and expansion takes place, the left ventricle (LV) fills with blood. The individual cells 12 are spaced from each other within the contractile jacket 10. Depending upon the size of the patient's heart and heart functions, the space between the cells may range from about 1 to about 2 mm. The result of contraction and expansion of the jacket 10 is that the heart works more efficiently in both systole and diastole. Communication between the cells is by connecting appendages 18 at each angle of the hexagon as shown in FIG. 3. All communication is bidirectional between the cells, allowing the cells to function in unison.

Insulating Layer

The external layer which surrounds the inner layer is preferably made of a conductive electro-active polymer which prevents electro-magnetic interference from external sources and prevents external noise from causing disturbances in the magnetic field, it preferably covers the inner jacket completely as shown in FIG. 1. While the external layer may move with the contractile layer, it does not contribute to expansion or contraction of the inner layer; it functions as a barrier to magnetic interference from outside sources, and as a barrier to interference from external noise. The inner layer and the outer layer are preferably bonded together at the base of the heart.

Microprocessor

The microprocessor 20 controls the operation of the jacket 10. It can receive signals from the LV, RV, or RA, and monitor all hemodynamic parameters. These signals are evaluated by the computer 23, and the hemodynamic variables assessed. The response of the computer 23 back to the magnetic cells is in real time. In the event a permanent pacemaker 25 has been implanted, the microprocessor 20 processes information received from the pacemaker 25 and coordinates it with the parameter received from the heart. In patients with heart block, or weak electrical signals, a two chamber, AV sequential pacemaker is required. In cases of long standing heart failure, a three chamber pacemaker may be needed to provide information to the microcomputer 23. The present technique to evaluate pacemaker performance is to place a magnet, on the skin, over the implanted unit. The insulating layer of the jacket will prevent this magnet from interfering with the function of the cells in the inner jacket.

The microcomputer 20 synchronizes the contraction and expansion of the inner jacket to the electrocardiogram (EKG) signals. The EKG signals need to be of sufficient electrical strength, whether a pacemaker 25 is inserted or not, to send correct information to the microcomputer 20 as shown in FIG. 5. When information is sent to the inner jacket, all of the cells contract or expand simultaneously. The PORST complex of the EG must be of sufficient strength to send signals to the microcomputer 20 and to work efficiently in regulating expansion and contraction of the jacket. The P wave represents atrial repolarization, the ORS represents ventricular repolarization, the T wave, preceded by a plateau, represents ventricular repolarization. There is a resting phase, and then the PORST begins again. If the rhythm is irregular or the EKG complexes are not electrically strong, a pacemaker 25 is inserted.

The microcomputer 20 outer shell or housing is manufactured to meet the same biocompatible standards as cardiac pacemakers, so it can be implanted subcutaneously in the body.

Battery or Power Supply

The power supply 21 is connected to the microprocessor 20. Relatively, the power demands of this system are low. It is estimated that, because the power demands of nanotechnology are low, that the battery will only require recharging after several hours. This will allow freedom of movement for the patient. The charge could even last several days. When recharging of the battery 22 is required, it is achieved by external means, through the skin, and the process is relatively fast.

As with other components of this system, the battery shell is enclosed in completely biocompatible material, and like the pacemaker, is designed to strict specifications so it can be implanted in the body.

The patient is free to move about, is not dependent on electrical outlets, and does not have to carry a heavy battery pack around. The recharging unit is small and wireless.

Advantages and Importance of the System

One of the major advantages of the devices and systems embodying features of the invention is that it functions interactively according to the hemodynamic needs of the body, Contraction and expansion of the jacket is calculated in real time to assist systolic and diastolic function, it utilizes nanotechnology so power demands are low, and it is made of biocompatible materials so all components of the system can be safely implanted as shown in FIG. 5.

The present system has little or no interface with the blood, which could raise issues with the coagulation system, and there are no ports leading outside the body, which could lead to a route for infection to enter.

Patients can be completely ambulatory. Since the life of the battery is long, frequent recharging is not required and there are no heavy battery packs to carry around. This contributes to a better quality of life.

Expensive monitoring of hemodynamic parameters is not required. The microprocessor 20 monitors, and prints out, when interrogated, any or all information regarding cardiac function. This includes LVEDP, LV end systolic pressure, RV end diastolic pressure, RV end systolic pressure, LV volume, RV volume, cardiac output, cardiac tension, ejection fraction, systolic and diastolic blood pressure, and heart rate. Monitoring is continuous, in real time, and the system immediately responds to changes in cardiac hemodynamics and makes appropriate adjustments.

The system is also cost effective in terms of initial insertion costs, subsequent hospitalizations, and hospital costs. Advances in engineering and technology have extended the average life of an implanted pacemaker to now be about ten years. It is estimated that this system will have the same life expectancy before components must be changed. This is a huge financial saving, and also contributes to quality of life.

This is a unique approach to the treatment of heart failure. After the jacket is installed, which requires limited thoracotomy, inserting the microcomputer and battery is accomplished at the same time, or later, using local anesthesia. Changing the pacemaker and battery, when required, can be done as same day admission under local anesthesia. The jacket should have an unlimited working capacity. As with pacemakers, replacement of the battery and microcomputer might be required, but would be infrequent, perhaps ten years. Because the system is versatile, relatively non invasive after the jacket is implanted and programmable it can be used in more than end stage heart failure, but is also suitable for moderate forms of the disease.

While particular forms of the invention have been illustrated and described herein, it will be apparent that various modifications and improvements can be made to the invention. For example, the embodiment described herein is primarily directed to a cardiac jacket with hexagonal shaped contractile cells. Other orientations of the electrically conductive coils may be employed. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "manufacture", "portion", "section", "steps" and words of similar import when used herein shall not be construed as invoking the provisions of 35 U.S.C. §112(6) unless the following claims expressly use the terms "means for" or "step for" followed by a particular function without reference to a specific structure or action.

All patents and patent applications referred to above are hereby incorporated herein by reference in their entirety.

What is claimed is:

1. A cardiac jacket for augmenting expansion and contraction of a heart, comprising a polymeric layer configured to fit about a portion of the heart and a plurality of hexagonal shaped contractile cells incorporated within or secured to the polymeric layer, each of the contractile cells having
   a. a nucleus comprising a periphery defined at least in part by a first electrically conductive coil
   b. an inner core comprising a periphery defined by a second electrically conductive coil spaced outwardly from the first electrically conductive coil and
   c. an outer core comprising a periphery defined at least in part by a third electrically conductive coil
   wherein the contractile cells are configured to pass electrical current through the first electrically conductive coil in a first current direction to generate a first magnetic field in a first magnetic direction and to pass electrical current through the second electrically conductive coil in the same first current direction as the first electrically conductive coil to generate a second magnetic field in the same magnetic direction as the first magnetic field and to pass electrical current through the second electrically conductive coil in a second current direction opposite to the first current direction to generate a second magnetic field in a second magnetic direction opposite to the first magnetic direction.

2. The jacket of claim 1 wherein each contractile cell has at least one conductive appendage coupled thereto.

3. The jacket of claim 2 wherein the conductive appendages are configured to conduct information to and from the contractile cells.

4. The jacket of claim 1 wherein the first, second and third electrically conductive coils define the hexagonal shape of the contractile cells.

5. The jacket of claim 1 wherein the electrically conductive coils are formed of nanowires.

6. The jacket of claim 5 wherein the nanowires have transverse dimensions between about 30 and 200 nanometers.

7. The jacket of claim 5 wherein the electrically conductive coils are helically shaped and have outer transverse dimensions of about 200 nanometers to 10 micrometers.

8. The jacket of claim 5 wherein the nanowires comprise platinum or conductive platinum alloys.

9. The jacket of claim 1 including an outer insulating layer disposed above the polymeric layer.

10. The jacket of claim 1 wherein the contractile cells are configured to pass electrical current through the first electrically conductive coil in a first current direction to generate a first magnetic field in a first magnetic direction and to pass electrical current through the second electrically conductive coil in the first current direction as the first electrically conductive coil to generate a second magnetic field in the same magnetic direction as the first magnetic field and to pass electrical current through the second electrically conductive coil in a second current direction opposite to the first current direction to generate a second magnetic field in a second magnetic field in a direction opposite to the first magnetic field.

* * * * *